US010512680B2

(12) United States Patent
Jordan et al.

(10) Patent No.: US 10,512,680 B2
(45) Date of Patent: *Dec. 24, 2019

(54) METHOD OF MAKING A MYCOPLASMA VACCINE

(71) Applicant: Boehringer Ingelheim Vetmedica GmbH, Ingelheim am Rhein (DE)

(72) Inventors: Dianna M. Murphy Jordan, Ames, IA (US); Brian Thomas Martinson, Duncombe, IA (US); Christine Margaret Muehlenthaler, Ames, IA (US); Axel Neubauer, St. Joseph, MO (US); Arun V. Iyer, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,342

(22) Filed: Jan. 19, 2016

(65) Prior Publication Data
US 2016/0136254 A1    May 19, 2016

Related U.S. Application Data

(63) Continuation of application No. 14/135,796, filed on Dec. 20, 2013, now Pat. No. 9,273,281.

(60) Provisional application No. 61/746,997, filed on Dec. 28, 2012.

(51) Int. Cl.
| G01N 33/554 | (2006.01) |
| A61K 39/02 | (2006.01) |
| C12N 1/20 | (2006.01) |
| C12N 1/36 | (2006.01) |
| C12N 5/071 | (2010.01) |
| A61K 39/00 | (2006.01) |

(52) U.S. Cl.
CPC ............ A61K 39/0241 (2013.01); C12N 1/20 (2013.01); C12N 1/36 (2013.01); C12N 5/0686 (2013.01); A61K 2039/521 (2013.01); A61K 2039/552 (2013.01); A61K 2039/55566 (2013.01); C12N 2502/70 (2013.01)

(58) Field of Classification Search
None
See application file for complete search history.

(56) References Cited

U.S. PATENT DOCUMENTS

| 3,917,819 | A | 11/1975 | Yoshioka et al. |
| 7,018,638 | B2 | 3/2006 | Chu et al. |
| 7,169,394 | B2 | 1/2007 | Chu et al. |
| 7,381,414 | B2 | 6/2008 | Lin et al. |
| 7,622,124 | B2 | 11/2009 | Chu et al. |
| 7,666,439 | B2 | 2/2010 | Chu et al. |
| 7,959,927 | B2 | 6/2011 | Chu et al. |
| 8,112,663 | B2 | 2/2012 | S et al. |
| 8,187,588 | B2 | 5/2012 | Chu et al. |
| 8,444,989 | B1 | 5/2013 | Ohnesorge et al. |
| 8,852,613 | B2 | 10/2014 | Ohnesorge et al. |
| 9,273,281 | B2 | 3/2016 | Jordan et al. |
| 9,650,600 | B2 | 5/2017 | Galvin et al. |
| 9,650,601 | B2 | 5/2017 | Nitzel et al. |
| 9,662,385 | B2 | 5/2017 | Dominowski et al. |
| 2003/0064079 | A1 | 4/2003 | Goudie et al. |
| 2003/0109473 | A1 | 6/2003 | Keich et al. |
| 2005/0013823 | A1 | 1/2005 | Keich et al. |
| 2005/0037027 | A1* | 2/2005 | Lin .................... A61K 39/0241 424/248.1 |
| 2008/0185755 | A1 | 8/2008 | Deaville et al. |
| 2009/0042814 | A1 | 2/2009 | Petyaev et al. |
| 2012/0213816 | A1 | 8/2012 | Chu et al. |
| 2013/0052717 | A1 | 2/2013 | Liu et al. |
| 2013/0230558 | A1 | 9/2013 | Ohnesorge et al. |
| 2013/0266601 | A1 | 10/2013 | Galvin et al. |
| 2013/0266602 | A1 | 10/2013 | Nitzel et al. |
| 2013/0266603 | A1 | 10/2013 | Nitzel et al. |
| 2014/0186393 | A1 | 7/2014 | Jordan et al. |
| 2014/0186394 | A1 | 7/2014 | Jordan et al. |
| 2014/0370058 | A1 | 12/2014 | Ohnesorge et al. |

FOREIGN PATENT DOCUMENTS

| CN | 102258776 A | 11/2011 |
| EP | 1260581 A1 | 11/2002 |
| EP | 1862537 A1 | 12/2007 |
| GB | 1074920 A | 7/1967 |
| GB | 1137306 A | 12/1968 |
| GB | 1439407 A | 6/1976 |
| JP | H11507225 A | 6/1999 |
| JP | 2001278808 A | 10/2001 |

(Continued)

OTHER PUBLICATIONS

Neyrolles et al. Microbiology vol. 144, pp. 1247-1255, 1998.*
Abstract and Claims in English for CN102258776, 2011.
Bhogal et al., "Production of mycoplasma-specific antisera in rabbits immunologically tolerized at birth to mycoplasma medium constituents". Journal of Immunological Methods, vol. 97, No. 2, 1987, pp. 191-199.
Gaush et al., "Characterization of an Established Line of Canine Kidney Cells (MDCK). *1 (31293)". Proceedings of the Society for Experimental Biology & Medicine, vol. 122, No. 3, Jul. 1966, pp. 931-935.
Imura et al., "An Immunoelectron Microscopic Study of Mycoplasma Hyosynoviae in Primary Swine Kiney Cell Culture". Kobe Journal of Medical Sciences, vol. 29, No. 1, 1983, pp. 1-15.

(Continued)

Primary Examiner — Jana A Hines
Assistant Examiner — Khatol S Shahnan Shah
(74) Attorney, Agent, or Firm — Judy Jarecki-Black

(57) ABSTRACT

The present invention relates to a method for the preparation of an immunogenic composition for the treatment and/or prophylaxis of mycoplasma infections in a subject comprising the cultivation of mycoplasma bacteria in a serum-reduced or swine serum-free, eukaryotic cell system; obtaining an antigen of the mycoplasma bacteria; and addition of a pharmaceutically acceptable carrier. Further, the present invention relates to the immunogenic composition obtainable by said method and a method for immunizing a subject comprising the administration of said immunogenic composition to a subject.

11 Claims, No Drawings

(56) References Cited

FOREIGN PATENT DOCUMENTS

| | | |
|---|---|---|
| JP | 2011243189 A | 12/2011 |
| WO | 1993016726 A2 | 9/1993 |
| WO | 199639629 A1 | 12/1996 |
| WO | 2002049666 A2 | 6/2002 |
| WO | 2003004052 A1 | 1/2003 |
| WO | 2003017755 A2 | 3/2003 |
| WO | 2009036241 A1 | 3/2009 |
| WO | 2009058833 A2 | 5/2009 |
| WO | 2009061798 A1 | 5/2009 |
| WO | 2009126356 A2 | 10/2009 |
| WO | 2009142086 A1 | 11/2009 |
| WO | 2010051210 A1 | 5/2010 |
| WO | 2010132932 A1 | 11/2010 |
| WO | 2011075379 A1 | 6/2011 |
| WO | 2013152081 A1 | 10/2013 |
| WO | 2013152083 A2 | 10/2013 |
| WO | 2014105671 A1 | 7/2014 |
| WO | 2014105672 A1 | 7/2014 |

OTHER PUBLICATIONS

International Search Report and Written Opinion for PCT/US2013/076803 dated Mar. 27, 2014.

Kobayashi et al., "Marolide Susceptibility of Mycoplasma hyorhinis Isolated from Piglets". Antimicrobial Agents and Chemotherapy, vol. 40, No. 4, Apr. 1995, pp. 1030-1032.

Kobisch et al., "Swine Mycoplasmoses". Review Scientifique Et technique De L'OFfice International Des Epizooties, vol. 15, No. 4, 1996, pp. 1569-1605.

Mochizuki, Masami, "Growth characteristics of canine pathogenic viruses in MDCK cells cultured in RPMI 1640 medium without animal protein". Vaccine, vol. 24, 2006, pp. 1744-1748.

Potgieter et al., "Chronological Development of Mycoplasma hyorhinis and Mycoplasma hyosynoviae Infections in Cultures of a Swine Synovial Cell Strain". Canadian Journal of Comparative Medicine—Revue Canadienne Demedecine Comparee, vol. 36, No. 2, Apr. 1972, pp. 145-149.

Sobko et al., "Development of Scientific Techniques for the Prevention of Mycoplasma Infections in Swine". Archiv Fuer Experimentelle Veterinaermedizin, vol. 43, No. 5, Jan. 1989, pp. 645-655. (Abstract in English on p. 654).

Volokhov et al., "Biological Enrichment of Mycoplasma Agents by Cocultivation with Permissive Cell Cultures". Applied and Environmental Microbiology, vol. 74, No. 17, Sep. 2008, pp. 5383-5391.

Volokhov et al., "Mycoplasma testing of cell substrates and biologics: Review of alternative non-microbiological techniques". Molecular and Cellular Probles, vol. 25, 2011, pp. 69-77.

Abstract in English for JP2001278808, 2001.

Draganov et al., "Mccoy and Mccoy-Plovdiv Cell Lines in Experimental and Diagnostic Practice—Past, Present and Perspectives." Journal of Culture Collections, vol. 4, 2004-2005, pp. 3-16.

Okada et al., "Cytological and immunological changes in bronchoalveolar lavage fluid and histological observation of lung lesions in pigs immunized with Mycoplasma hyopneumoniae inactivated vaccine prepared from broth culture supernate." Vaccine, vol. 18, 2000, pp. 2825-2831.

Xiong et all., "Immune Study of a Intramuscular Injected Live Vaccine against Mycoplasma hyopneumoniae Enhanced by Different Adjuvants." China Animal Husbandry & Veterinary Medicine, vol. 38, No. 10, 2011, pp. 163-168. (English Abstract at p. 168).

Zhang et al., "Research advance in vaccines against important mycoplasmal diseases in livestock." Chinese Veterinary Science, vol. 41, No. 12, 2011, pp. 1314-1320. (Abstract in English on p. 1314).

Abstract in English for WO2009142086, 2009.

Kim et al., "Comparative efficacy of commercial Mycoplasma hyopneumoniae and porcine circovirus 2 (PCV2) vaccines in pigs experimentally infected with M. hyopneumoniae and PCV2." Vaccine, vol. 29, 2011, pp. 3206-3212.

Lauritsen et al., "Testing immunogenicity of Mycoplasma hyosynoviae vaccine candidates: Induction of antibodies and IFN-gamma response." Veterinary Immunology and Immunopathology, vol. 128, 2009, pp. 329.

Pfizer Animal Health, "RespiSure1ONE: From Day 1, RespiSure-ONE® offers more flexibility and the start of exceptional M. hyopneumoniae protection." 2010, pp. 1-2. [Accessed at https://www.zoetisus.com/_locale-assets/mcm-portal-assets/my-resources/respisureoneproductsheet.pdf on Dec. 15, 2017].

* cited by examiner

METHOD OF MAKING A MYCOPLASMA VACCINE

BACKGROUND

Bacteria of the *Mycoplasma* genus belong to the class Mollicutes and represent a group of organisms that derived from the Firmicutes lineage. Mollicutes are the smallest autonomously replicating organisms, which differ structurally from other eubacteria in that they lack a cell wall. The surface of their single membrane is considered a key interface in mediating adaptation and survival in the context of a complex, immunocompetent host. Further, Mollicutes have a small genome and a limited number of metabolic pathways. Therefore, members of the *Mycoplasma* genus have also been portrayed as "minimal self-replicating organisms." However, despite this apparent simplicity, a large number of mycoplasma bacteria are pathogens of humans and a wide range of animals. In contrast to other pathogenic bacteria where virulence is mostly determined by toxins, invasins, and cytolysins, pathogenic *Mycoplasma* bacteria appear to have no such typical primary virulence factors (Chambaud, I. et al, 2001, *Nucleic Acids Res.* 29: 2145-2153, Fraser et al, 1995, *Science* 270: 397-403). There is currently little knowledge available on the molecular mechanisms and the effectors that allow pathogenic mycoplasmas to cause host cell damage, inflammation and disease.

Pathogenic *Mycoplasma* bacteria cause mainly atypical pneumonia, uro-genital infections and arthritis in humans and in animals (Blanchard, A., and G. F. Browning (eds.). 2005. *Mycoplasmas: Molecular biology, pathogenicity and strategies for control. Horizon Bioscience*, Wymondham U. K.; Kobisch M. and Friis N. F. 1996, *Swine mycoplasmoses, Rev. Sci. Tech. Off. Int. Epiz.* 15, 1569-1605). It is known that reactivation or exacerbation of the signs repeats and transfers gradually to a chronic disease, and thus along with early diagnosis and early treatment, prevention or treatment of exacerbation or reactivation are important. *M. hyopneumoniae* is the aetiological agent of enzootic pneumonia. In swine it is one of the most common and economically important diseases due to reduced weight gain and poor feed efficiency. The disease causes lesions in the lungs, a chronic cough, dull hair coat, retarded growth and unthrifty appearance lasting several weeks. The lung lesions, particularly in ventral apical and cardiac lobes, are characterized by a hyperplasia of the epithelial cells and an increased perivascular and peribronchiolar accumulation of mononuclear cells. *M. hyorhinis*, another common mycoplasma of the respiratory tract of pigs, can cause polyserositis and arthritis in piglets. *M. hyosynoviae* is generally located in the tonsils and can cause arthritic disease, leading to economic losses. *M. hyosynoviae* is isolated from the joints and pharyngeal/tonsillar samples and can induce antibodies in blood and joint fluid. *M. bovis* is considered to be one of the more pathogenic bacteria of *Mycoplasma* and causes significant economic losses worldwide. *Mycoplasma* bacteria cause severe clinical signs in cattle of all ages. *M. bovis* is the most frequent *Mycoplasma* pathogen found to cause pneumonia, mastitis, and arthritis in cattle and its etiological role has also been associated with otitis, keratoconjunctivitis, synovitis, and reproductive disorders in cows and bulls.

Because mycoplasma lack a cell wall, they are unaffected by many common antibiotics such as penicillin or other beta-lactam antibiotics that target cell wall synthesis. Therapeutic agents for mycoplasma infection that are in practical use are some antibiotics such as macrolide-based, or new quinolone-based, or tetracycline-based antibiotics, but such antibiotics have great adverse effects such as advent of drug-resistant strains, which leads the mycoplasma infection to become severe while sufficient treating effects are not expected, and becomes a cause for transfer to a chronic disease. Further, vaccination is an effective method of controlling mycoplasma infection. However, significant high yields of mycoplasma needed for the preparation of vaccines are obtained by cultivation normally only in complex media (Kobisch M. and Friis N. F. 1996, *Swine mycoplasmoses, Rev. Sci. Tech. Off. Int. Epiz.* 15, 1569-1605; Gabridge M. G. et al. 1976, *Cultivation of mycoplasma in a modified tissue culture medium, Applied and Environmental microbiology.* 31, 986-989; Sotoodehnia A. Et al 2007, *Preparation of agalactia vaccine in fermentor, Archives of razi institute,* 62, 45-48; Dahlia et al., 2009 *Isolation of Mycoplasma hyosynoviae from pneumonic lung of swine, Tropical Biomedicine* 26-341-345). Dependent on the mycoplasma bacteria to be cultivated, the complex media are supplemented with 10-30% serum and sometimes with yeast extract. Thus, due to the high price of serum the cultivation of mycoplasma bacteria is cost intensive. Further, a reduction of serum in the complex media would be beneficial in light of animal welfare, too. Thus, there is a need for the cultivation of significant high yields of mycoplasma in a serum-reduced culturing system for the preparation of immunogenic compositions effective in preventing mycoplasma infection. Moreover, the swine specific mycoplasma bacteria are generally cultivated in complex media containing swine specific serum (Kobisch M. and Friis N. F. 1996, *Swine mycoplasmoses, Rev. Sci. Tech. Off. Int. Epiz.* 15, 1569-1605). However, swine specific serum can contain other swine-specific pathogens or can contain antibodies against swine specific pathogens which can cause a reduced immunogenicity of the immunogenic composition to be prepared. Thus, there is also a need for the cultivation of significant high yields of mycoplasma in a swine serum-free culturing system for the preparation of immunogenic compositions effective in preventing mycoplasma infection.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "a or an antigen" includes a plurality of antigens, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art.

Generally, the present invention provides a method for the preparation of an immunogenic composition for the treatment and/or prophylaxis of mycoplasma infections in a subject comprising a) cultivation of mycoplasma bacteria in a serum-reduced, eukaryotic cell system; b) obtaining an antigen of the mycoplasma bacteria; and c) addition of a pharmaceutically acceptable carrier.

Advantageously, the experimental data provided by the present invention disclose that mycoplasma bacteria can be produced in a serum-reduced, eukaryotic cell system.

The term "immunogenic composition" refers to a composition that comprises at least one antigen, which elicits an immunological response in the host to which the immunogenic composition is administered. Such immunological response can be a cellular and/or antibody-mediated immune response to the immunogenic composition of the invention. The host is also described as "subject". Preferably, any of the hosts or subjects described or mentioned herein is an animal.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutic response.

A "protective immunological response" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

An "antigen" as used herein refers to, but is not limited to, components which elicit an immunological response in a host to an immunogenic composition or vaccine of interest comprising such antigen or an immunologically active component thereof. The antigen or immunologically active component can be a microorganism that is whole (in inactivated or modified live form), or any fragment or fraction thereof, which, if administered to a host, can elicit an immunological response in the host. The antigen can be or can comprise complete live organisms in either its original form or as attenuated organisms in a so called modified live vaccine (MLV). The antigen can further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen can comprise whole organisms inactivated by appropriate methods in a so called killed vaccine (KV). If the organism is a bacterium, the killed vaccine is called a bacterin.

The term "treatment and/or prophylaxis" refers to the lessening of the incidence of the particular mycoplasma infection in a herd or the reduction in the severity of clinical signs caused by or associated with the particular mycoplasma infection. Thus, the term "treatment and/or prophylaxis" also refers to the reduction of the number of animals in a herd that become infected with the particular mycoplasma bacteria (=lessening of the incidence of the particular mycoplasma infection) or to the reduction of the severity of clinical signs normally associated with or caused by a mycoplasma infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to a subject or herd of subjects in need of or that could benefit from such a treatment/prophylaxis. The term "treatment" refers to the administration of the effective amount of the immunogenic composition once the subject or at least some animals of the herd is/are already infected with such mycoplasma and wherein such animals already show some clinical signs caused by or associated with such mycoplasma infection. The term "prophylaxis" refers to the administration of a subject prior to any infection of such subject with mycoplasma or at least where such animal or none of the animals in a group of animals do not show any clinical signs caused by or associated with the infection by such mycoplasma.

The term "an effective amount" as used herein means, but is not limited to an amount of antigen, that elicits or is able to elicit an immune response in a subject. Such effective amount is able to lessen the incidence of the particular mycoplasma infection in a herd or to reduce the severity of clinical signs of the particular mycoplasma infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to subjects that are either not treated or treated with an immunogenic composition that was available prior to the present invention but subsequently infected by the particular mycoplasma bacteria.

The term "clinical signs" as used herein refers to signs of infection of a subject from mycoplasma bacteria. The clinical signs of infection depend on the pathogen selected. Examples for such clinical signs include but are not limited to respiratory distress, polyserositis (such as peritonitis, pleuritis, pericarditis), arthritis (lameness and swollen joints), otitis, roughened hair coat, slight fever, depression, reduced appetite, and bacteremia. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight gain or loss, dehydration, diarrhea, joint swelling, lameness, wasting, paleness of the skin, unthriftiness, diarrhea, and the like.

Reducing the incidence of or reducing the severity of clinical signs caused by or being associated with the particular mycoplasma infection in a subject can be reached by the administration of one or more doses of the immunogenic composition of the present invention to a subject in need. As demonstrated by the Examples 2 and 3, the immunogenic composition as provided herein has been proven to be efficacious after the administration of a single dose to a subject of need.

The term "infection" or "infected" refer to the infection of a subject by a pathogen, i.e. *M. hyorhinis* or *M. hyorhinis* and *M. hyosynoviae* or *M. hyorhinis, M. hyopneumoniae* and *M. hyosynoviae*.

The term "mycoplasma" is known by the person skilled in the art. "*Mycoplasma*" refers to a genus of bacteria, e.g. as described in Blanchard, A., and G. F. Browning (eds.). 2005. *Mycoplasmas: Molecular biology, pathogenicity and strategies for control. Horizon Bioscience,* Wymondham U. K.; Kobisch M. and Friis N. F. 1996, *Swine mycoplasmoses, Rev. Sci. Tech. Off. Int. Epiz.* 15, 1569-1605. Bacteria can be classified based on their biochemical and microbiological properties as well as their morphology. These classification criteria are well known in the art. In general the mycoplasma infection is associated with the clinical signs described elsewhere in this description.

The term "mycoplasma" as used herein refers to *M. hyorhinis* or *M. hyorhinis* and *M. hyosynoviae* or *M. hyorhinis, M. hyopneumoniae* and *M. hyosynoviae*. However, the term mycoplasma also encompasses *M. bovis*. Complete genome sequence of *M. hyorhinis* is exemplarily provided e.g. by Liu, W. et al., *J. Bacteriol.* 2010, vol. 192 (21), 5844-45 doi: 10.1128/JB.00946-10. Epub 2010 Aug. 27 or by Calcutt M J. et al., 2012, *J. Bacteriol. Vol.* 194 (7), 1848 doi: 10.1128/JB.00033-12. Isolates of *M. hyosynoviae* are exemplarily deposited at the American Tissue Culture Collection under accession numbers ATCC 25591 or ATCC 27095. Isolates of *Mycoplasma hyopneumoniae* are exemplarily deposited at the American Tissue Culture Collection under accession numbers ATCC 25095, ATCC 25617, and ATCC 25934. The genomic DNA of *Mycoplasma hyopneumoniae* J-strain is deposited at the American Tissue Culture Collection under accession numbers ATCC 25934D. Isolates of *Mycoplasma bovis* are well known to a person skilled in the art and some isolates are exemplarily deposited at the American Tissue Culture Collection under accession numbers ATCC 25025, ATCC 25523, and ATCC 27368.

The term "cultivation" is known by the person skilled in the art. The term relates to the propagation of cells in culture outside the organism. Particularly, the term "cultivation" relates to the propagation of cells outside the organism in a cell system.

The term "cell system" is known by the person skilled in the art. In particular, the term "cell system" is an in vitro cell culture system for the cultivation of microorganism, such as e.g. mycoplasma bacteria. Such cell system comprises host cells and cell culture medium suitable for the propagation of such cells outside of the organism. In particular, the host cells may or may not be susceptible for an infection with the mycoplasma bacteria. Such host cells can be present as live cells, in inactivated form or as cell fragments. Preferably, such host cells are eukaryotic cells of a eukaryotic cell system.

The term "eukaryotic cell system" comprises primary eukaryotic cells and eukaryotic cells derived from multicellular organisms such as plants or animals. Furthermore, eukaryotic cell system encompasses eukaryotic single cell organisms (also referred to as microorganisms), e.g. bacteria or fungi including yeast. However, it is understood the eukaryotic cells are different from mycoplasma bacteria. Eukaryotic host cells that can be used to practice the method as described herein include but are not limited to Madin-Darby Canine Kidney Epithelial (MDCK) cells (e.g. Madin-Darby Canine Kidney Epithelial Cells as deposited with the American Tissue Culture Collection under accession number ATCC CCL-34 or ATCC CRL-2285) or McCoy cells (e.g. as deposited with the American Tissue Culture Collection under accession number ATCC CRL-1696).

The term "cell free cultivation system" as used herein refers to cultivation system that does not include any cells except of the mycoplasma bacteria.

The term "serum reduced" refers to a reduced amount of serum that is added for the cultivation of mycoplasma bacteria in the eukaryotic cell system compared to the amount of serum that is used for the cultivation of mycoplasma bacteria of the same species in a cell free cultivation system. The amount of serum for the cultivation of mycoplasma bacteria in the eukaryotic cell system compared to the amount of serum for the cultivation of mycoplasma bacteria in a cell free cultivation system is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95%, even more preferably by at least 96%, even more preferably by at least 97%, even more preferably by at least 98%, even more preferably by at least 99%, most preferably by 100%. Thus, it has to be understood that according to the present invention the mycoplasma bacteria are most preferably cultivated in a eukaryotic cell system lacking any serum.

Preferred amounts of serum for the cultivation of mycoplasma bacteria in the eukaryotic cell system include serum concentrations between about 0-10% (v/v), more preferably from about 1-9% (v/v), still more preferably from about 1-8% (v/v), even more preferably from about 1-7% (v/v), even more preferably from about 1-6% (v/v), and most preferably about 2-5% (v/v).

Preferred amounts of serum for the cultivation of mycoplasma bacteria in the eukaryotic cell system comprising MDCK cells include serum concentration between about 0-6% (v/v), more preferably from about 1-5% (v/v), still more preferably from about 2-4% (v/v), even more preferably from about 2-3% (v/v), and most preferably about 2% (v/v).

Preferred amounts of serum for the cultivation of mycoplasma bacteria in the eukaryotic cell system comprising McCoy cells include serum concentration between about 0-10% (v/v), more preferably from about 1-9% (v/v), still more preferably from about 2-8% (v/v), even more preferably from about 3-7% (v/v), even more preferably from about 4-6% (v/v), and most preferably about 5% (v/v).

In accordance with one aspect of the present invention it is to be understood that the eukaryotic cells of the eukaryotic cell system are to be infected with mycoplasma bacteria. The infection of eukaryotic cells by mycoplasma bacteria and the conditions of the post incubation period are well known to the person skilled in the art. However, preferably, post transfection the cells are incubated over a period of up to 21 days, more preferably from about two days to about fourteen days, more preferably from about two days to about eight days, still more preferably from about three to five days. Preferred incubation conditions include a temperature between about 32-42° C., more preferably from about 34-40° C., still more preferably from about 35-39° C., even more preferably from about 36-38° C., and most preferably about 37° C. Preferred incubation conditions also include a $CO_2$-concentration between about 2% to 8%, more preferably from about 3% to 7% even more preferably from about 4% to 6%, and most preferably about 5%. Preferably, the eukaryotic cells are observed following transfection for characteristic changes, such as cell density trends, the decrease in viability including cytopathic effects during the post-infection period and the color change of the medium due to pH-changes.

The term "obtaining" comprises the harvest, isolation, purification and/or formulation (e.g. finishing, inactivation and/or blending) of the antigen.

The term "harvest" refers to collecting or recovering the antigen of the mycoplasma bacteria from the transfected eukaryotic cell system. Any conventional method known in the art can be used to recover said mycoplasma antigen, e.g. any separation method. Well known methods in the art comprise centrifugation or filtration, such as using a semipermeable membrane having a certain pore size.

The term "isolation" comprises an isolation step of the mycoplasma antigen. Methods for the isolation of antigens of the mycoplasma bacteria from the infected eukaryotic cell system are known to a person skilled in the art. Those methods comprise physical and/or chemical methods, including but are not limited to freeze thaw cycles, treatment with ultrasound and the alike.

Methods for the "purification" of antigens from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The antigen can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein can also include further finishing steps as part of the final formulation process, like the addition of buffer, inactivation, neutralization steps and the alike.

Any conventional "inactivation" method can be used for purposes of the present invention. Thus, inactivation can be performed by chemical and/or physical treatments which are known to the person skilled in the art. Preferred inactivation methods include the addition cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation can also comprise a neutralization step. Preferred neutralization agents include but are not limited to sodium thiosulfate, sodium bisulfite and the alike.

Preferred formalin inactivation conditions include formalin concentration from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the *mycoplasma* species. In general, the inaction process is performed until no mycoplasma growth can be detected in a suitable cultivation system.

According to a further aspect, the inactivated bacterin component of the invention can be incorporated into liposomes using known technology such as that described in *Nature*, 1974, 252, 252-254 or *Journal of Immunology*, 1978, 120, 1109-13. According to another aspect, the inactivated bacterin component of the invention can be conjugated to suitable biological compounds such as polysaccharides, peptides, proteins, or the like, or a combination thereof.

Thus, according to one aspect, the present application provides a method for the preparation of an immunogenic composition for the treatment and/or prophylaxis of mycoplasma infections in a subject comprising a) cultivation of mycoplasma bacteria in a serum-reduced, eukaryotic cell system; b) obtaining an antigen of the mycoplasma bacteria; and c) addition of a pharmaceutically acceptable carrier, wherein the immunogenic composition is a mycoplasma immunogenic composition.

In one aspect of the present invention the serum that is used for the cultivation of the mycoplasma bacteria is free of swine-serum. The term "free of swine-serum" means that no swine-serum is added during the cultivation process of the mycoplasma bacteria in the eukaryotic cell system.

Thus, according to one aspect, the present application provides a method for the preparation of an immunogenic composition for the treatment and/or prophylaxis of mycoplasma infections in a subject comprising a) cultivation of mycoplasma bacteria in a serum-reduced, eukaryotic cell system; b) obtaining an antigen of the mycoplasma bacteria; and c) addition of a pharmaceutically acceptable carrier, wherein the serum is free of swine-serum. According to a further aspect, all of the mycoplasma antigens are produced in a swine-serum free, eukaryotic cell system.

In a further aspect, the cultivation of the mycoplasma bacteria occurs in the absence of serum. This means, that no serum is added during the cultivation of the mycoplasma bacteria in the eukaryotic cell system. Thus, according to one aspect, the present application provides a method for the preparation of an immunogenic composition for the treatment and/or prophylaxis of mycoplasma infections in a subject comprising a) cultivation of mycoplasma bacteria in a eukaryotic cell system in the absence of serum; b) obtaining an antigen of the mycoplasma bacteria; and c) addition of a pharmaceutically acceptable carrier. According to a further aspect, all of the mycoplasma antigens are produced in the absence of serum.

In one aspect of the present invention the mycoplasma antigens is/are a whole inactivated mycoplasma bacterin. It is understood, that only one, some or all of the mycoplasma antigens can be whole inactivated mycoplasma bacterin.

Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the mycoplasma antigen is a whole inactivated bacterin. According to a further aspect, all of the mycoplasma antigens within the immunogenic composition are whole inactivated bacterins. The inactivated mycoplasma antigens can be obtained in such that step b) of the method described hereinabove includes an inactivation step. Thus, according to a further aspect, method is provided for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria and inactivating the mycoplasma antigens; and c) addition of a pharmaceutically acceptable carrier.

The whole inactivated bacterin can be obtained by the inactivation of whole mycoplasma bacteria, preferably by a method as described herein above. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria and inactivating the mycoplasma antigens; and c) addition of a pharmaceutically acceptable carrier, wherein the mycoplasma antigens are complete mycoplasma bacteria.

Preferably, the mycoplasma bacteria are inactivated with formalin as described hereinabove. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria and inactivating the mycoplasma antigens with formalin; and c) addition of a pharmaceutically acceptable carrier, wherein the mycoplasma antigens are complete mycoplasma bacteria. Preferably, the formalin is used in concentrations as described hereinabove.

In one aspect of the present invention the eukaryotic cell system comprises a MDCK cell line. The MDCK (Madin-Darby Canine Kidney Epithelial Cells) cell line was derived from the kidney tissue of an adult female cocker spaniel. However, the MDCK cell line is known to the person skilled in the art. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the eukaryotic cell system comprises a MDCK cell line. Again, the mycoplasma antigen can be whole inactivated mycoplasma bacterin, preferably inactivated with formalin.

In a further aspect of the present invention the eukaryotic cell system comprises a McCoy cell line. The McCoy cell line is known to the person skilled in the art. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the eukaryotic cell system comprises a McCoy cell line. Again, the mycoplasma antigen can be whole inactivated mycoplasma bacterin, preferably inactivated with formalin.

In one aspect of the present invention the mycoplasma bacteria are selected from the group consisting of: *M. hyopneumoniae, M. hyorhinis, M. hyosynoviae* and *M. bovis*. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the mycoplasma bacteria is selected from the group consisting of: *M. hyopneumoniae, M. hyorhinis, M. hyosynoviae* and *M. bovis*. Preferably the mycoplasma antigen can be whole inactivated mycoplasma bacterin, preferably inactivated with formalin. It is understood, that only one, some or all of the mycoplasma antigens can be whole inactivated bacterin.

In a further aspect of the present invention the mycoplasma bacteria are selected from the group consisting of: *M. hyopneumoniae, M. hyorhinis, M. hyosynoviae* and any combinations thereof. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the mycoplasma bacteria are selected from the group consisting of: *M. hyopneumoniae, M. hyorhinis, M. hyosynoviae* and any combinations thereof. Preferably the mycoplasma antigen can be whole inactivated mycoplasma bacterin, preferably inactivated with formalin. It is understood, that only one, some or all of the mycoplasma antigens can be whole inactivated bacterin.

Thus, according to one aspect, the present application provides a method for the preparation of an immunogenic composition for the treatment and/or prophylaxis of mycoplasma infections in a subject comprising a) cultivation of *M. hyopneumoniae* bacteria in a serum-reduced or swine serum free, eukaryotic cell system; b) obtaining an antigen of the *M. hyopneumoniae* bacteria; and c) addition of a pharmaceutically acceptable carrier. Preferably the antigen of *M. hyopneumoniae* is whole inactivated *M. hyopneumoniae* bacterin, preferably inactivated with formalin. It is understood, that only one, some or all of the *M. hyopneumoniae* antigens can be whole inactivated *M. hyopneumoniae* bacterin.

Thus, according to one aspect, the present application provides a method for the preparation of an immunogenic composition for the treatment and/or prophylaxis of mycoplasma infections in a subject comprising a) cultivation of *M. hyorhinis* bacteria in a serum-reduced or swine serum free, eukaryotic cell system; b) obtaining an antigen of the *M. hyorhinis* bacteria; and c) addition of a pharmaceutically acceptable carrier. Preferably the antigen of *M. hyorhinis* is whole inactivated *M. hyorhinis* bacterin, preferably inactivated with formalin. It is understood, that only one, some or all of the *M. hyorhinis* antigens can be whole inactivated *M. hyorhinis* bacterin.

Thus, according to one aspect, the present application provides a method for the preparation of an immunogenic composition for the treatment and/or prophylaxis of mycoplasma infections in a subject comprising a) cultivation of *M. hyosynoviae* bacteria in a serum-reduced or swine serum free, eukaryotic cell system; b) obtaining an antigen of the *M. hyosynoviae* bacteria; and c) addition of a pharmaceutically acceptable carrier. Preferably the antigen of *M. hyosynoviae* is whole inactivated *M. hyosynoviae* bacterin, preferably inactivated with formalin. It is understood, that only one, some or all of the *M. hyosynoviae* antigens can be whole inactivated *M. hyosynoviae* bacterin.

According to a further aspect, the immunogenic composition comprises mycoplasma antigen selected from the group consisting of: *M. hyopneumoniae, M. hyorhinis, M. hyosynoviae* and any combinations thereof. At least bacteria of one of the mycoplasma species as described above (e.g.

*M. hyopneumoniae* or *M. hyorhinis* or *M. hyosynoviae*) which are used for the preparation of the mycoplasma immunogenic composition are cultivated according to the invention in a serum-reduced or swine serum free, eukaryotic cell system. Preferably, all of the mycoplasma bacteria which are used for the preparation of the mycoplasma immunogenic composition are cultivated according to the invention in a serum-reduced or swine serum free, eukaryotic cell system.

Thus, according to one aspect, the present application provides a method for the preparation of an immunogenic composition which comprises mycoplasma antigen of *M. hyopneumoniae, M. hyorhinis, M. hyosynoviae* and/or any combinations thereof for the treatment and/or prophylaxis of mycoplasma infections in a subject comprising a) cultivation of at least one mycoplasma bacteria selected from the group consisting of: *M. hyopneumoniae, M. hyorhinis,* and *M. hyosynoviae* in a serum-reduced or swine serum free, eukaryotic cell system; b) obtaining an antigen of the mycoplasma bacteria; and c) addition of a pharmaceutically acceptable carrier. Preferably all of the mycoplasma bacteria are cultivated in a serum-reduced or swine serum free, eukaryotic cell system according to the invention. Preferably, at least one of the mycoplasma antigens is whole inactivated mycoplasma bacterin, preferably inactivated with formalin. It is understood, that only one, some or all of the mycoplasma antigens can be whole inactivated bacterin.

Thus, according to one aspect, the present application provides a method for the preparation of an immunogenic composition which comprises mycoplasma antigen of *M. hyopneumoniae, M. hyorhinis, M. hyosynoviae* and/or any combinations thereof for the treatment and/or prophylaxis of mycoplasma infections in a subject comprising a) cultivation of at least *M. hyopneumoniae* bacteria in a serum-reduced or swine serum free, eukaryotic cell system; b) obtaining an antigen of the mycoplasma bacteria; and c) addition of a pharmaceutically acceptable carrier. Preferably all of the *M. hyopneumoniae* bacteria are cultivated in a serum-reduced or swine serum free, eukaryotic cell system according to the invention. Preferably, at least one of the *M. hyopneumoniae* antigens is whole inactivated *M. hyopneumoniae* bacterin, preferably inactivated with formalin. It is understood, that only one, some or all of the *M. hyopneumoniae* antigens can be whole inactivated bacterin.

Thus, according to one aspect, the present application provides a method for the preparation of an immunogenic composition which comprises mycoplasma antigen of *M. hyopneumoniae, M. hyorhinis, M. hyosynoviae* and/or any combinations thereof for the treatment and/or prophylaxis of mycoplasma infections in a subject comprising a) cultivation of at least *M. hyorhinis* bacteria in a serum-reduced or swine serum free, eukaryotic cell system; b) obtaining an antigen of the mycoplasma bacteria; and c) addition of a pharmaceutically acceptable carrier. Preferably all of the *M. hyorhinis* bacteria are cultivated in a serum-reduced or swine serum free, eukaryotic cell system according to the invention. Preferably, at least one of the *M. hyorhinis* antigens is whole inactivated *M. hyorhinis* bacterin, preferably inactivated with formalin. It is understood, that only one, some or all of the *M. hyorhinis* antigens can be whole inactivated bacterin.

Thus, according to one aspect, the present application provides a method for the preparation of an immunogenic composition which comprises mycoplasma antigen of *M. hyopneumoniae, M. hyorhinis, M. hyosynoviae* and/or any combinations thereof for the treatment and/or prophylaxis of mycoplasma infections in a subject comprising a) cultivation of at least *M. hyosynoviae* bacteria in a serum-reduced or swine serum free, eukaryotic cell system; b) obtaining an antigen of the mycoplasma bacteria; and c) addition of a pharmaceutically acceptable carrier. Preferably all of the *M. hyosynoviae* bacteria are cultivated in a serum-reduced or swine serum free, eukaryotic cell system according to the invention. Preferably, at least one of the *M. hyosynoviae* antigens is whole inactivated *M. hyosynoviae* bacterin, preferably inactivated with formalin. It is understood, that only one, some or all of the *M. hyosynoviae* antigens can be whole inactivated bacterin.

In one aspect of the present invention the immunogenic composition is formulated for a single-dose administration. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the immunogenic composition is formulated for a single-dose administration. Preferably, at least one of the mycoplasma antigens is whole inactivated mycoplasma bacterin, preferably inactivated with formalin. It is understood, that only one, some or all of the mycoplasma antigens can be whole inactivated bacterin.

Advantageously, the experimental data provided by the present invention disclose that a single dose administration of the immunogenic composition of the present invention reliably and effectively stimulated a protective immune response. Specifically, a measurable antibody response has been shown for *M. hyorhinis* and *M. hyopneumoniae*.

The term "subject" as used herein relates to animals, preferably to mammals such as mice, rats, guinea pigs, rabbits, hamsters, swine, sheep, dogs, cats, horses, monkeys, or cattle and, also preferably, to humans.

In one aspect of the present invention the subject is a swine. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the subject is a swine. Preferably, at least one of the mycoplasma antigens is whole inactivated mycoplasma bacterin, preferably inactivated with formalin. It is understood, that only one, some or all of the mycoplasma antigens can be whole inactivated bacterin.

In a further aspect of the present invention the subject is cattle. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the subject is a cattle. Preferably, at least one of the mycoplasma antigens is whole inactivated mycoplasma bacterin, preferably inactivated with formalin. It is understood, that only one, some or all of the mycoplasma antigens can be whole inactivated bacterin.

In a further aspect of the present invention the subject is a cat. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the subject is a cat. Preferably, at least one of the mycoplasma antigens is whole inactivated mycoplasma bacterin, preferably inactivated with formalin. It is understood, that only one, some or all of the mycoplasma antigens can be whole inactivated bacterin.

In a further aspect of the present invention the subject is a dog. Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the subject is a dog. Preferably, at least one of the mycoplasma antigens is whole inactivated mycoplasma bacterin, preferably inactivated with formalin. It is understood, that only one, some or all of the mycoplasma antigens can be whole inactivated bacterin.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

In one aspect of the present invention the pharmaceutical-acceptable carrier is an adjuvant.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314, or muramyl dipeptide among many others. Among the copolymers of maleic anhydride and alkenyl derivative, the copolymers EMA (Monsanto), which are copolymers of maleic anhydride and ethylene, are included. The dissolution of these polymers in water leads to an acid solution that will be neutralized, preferably to physiological pH, in order to give the adjuvant solution into which the immunogenic, immunological or vaccine composition itself will be incorporated.

A further example of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are polymers of acrylic acid cross-linked with polyalkenyl ethers or divinyl glycol or cross-linked with an allyl sucrose or with allyl pentaerythritol. Among them, there may be mentioned CARBOPOL® 974P, 934P and 971P. Most preferred is the use of CARBOPOL® 971P.

Preferably, the adjuvant is added in an amount of about 100 μg to about 10 mg per dose. Even more preferably the adjuvant is added in an amount of about 100 μg to about 10 mg per dose. Still more preferably the adjuvant is added in an amount of about 500 μg to about 5 mg per dose. Still more preferably the adjuvant is added in an amount of about 750 μg to about 2.5 mg per dose. Most preferably the adjuvant is added in an amount of about 1 mg per dose.

In a preferred embodiment of the invention the adjuvant is selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymer, SAF-M, monophosphoryl lipid A, Avridine lipid-amine, heat-labile enterotoxin from E. coli (recombinant or otherwise), cholera toxin, IMS 1314, muramyl dipeptide, and combinations thereof.

Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the pharmaceutical-acceptable carrier is an adjuvant. Preferably, at least one of the mycoplasma antigens is whole inactivated mycoplasma bacterin, preferably inactivated with formalin. It is understood, that only one, some, or all of the mycoplasma antigens can be whole inactivated bacterin.

In one aspect of the present invention the pharmaceutically acceptable carrier is a water-in-oil-in-water emulsion or a carbomer. Thus, according to one aspect, the present application provides a method for the preparation of an immunogenic composition for the treatment and/or prophylaxis of mycoplasma infections in a subject comprising a)

cultivation of mycoplasma bacteria in a serum-reduced or swine serum free, eukaryotic cell system; b) obtaining an antigen of the mycoplasma bacteria; and c) addition of a pharmaceutically acceptable carrier, wherein the pharmaceutically acceptable carrier is a water-in-oil-in-water emulsion or a carbomer. Preferably, at least one of the mycoplasma antigens is whole inactivated mycoplasma bacterin, preferably inactivated with formalin. It is understood, that only one, some, or all of the mycoplasma antigens can be whole inactivated bacterin.

In one aspect of the present invention the water-in-oil-in-water emulsion is Montanide ISA207 VG. Montanide ISA207 VG is an adjuvant composed of oleic esters of anhydrous mannitol in solution in a non mineral oil and is designed to achieve water-in-oil-in-water vaccine emulsions. Montanide ISA207 VG is well known to the person skilled in the art and can be used.

Thus, according to one aspect, the present application provides a method for the preparation of an immunogenic composition for the treatment and/or prophylaxis of mycoplasma infections in a subject comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the pharmaceutically acceptable carrier is Montanide ISA207 VG or CARBOPOL®. Preferably, at least one of the mycoplasma antigens is whole inactivated mycoplasma bacterin, preferably inactivated with formalin. It is understood, that only one, some, or all of the mycoplasma antigens can be whole inactivated bacterin.

The present invention also relates to a method as described above for increasing the immunogenicity of a mycoplasma antigen. Advantageously, the experimental data provided by the present invention disclose that mycoplasma bacteria antigens provided by the above described method have an increased immunogenicity compared to antigens obtained from mycoplasma bacteria cultivated in a cell free culturing system. Specifically, MDCK-based *M. hyorhinis* vaccines showed earlier on-set of sero-conversion, greater number of sero-positive pigs and higher serological titers.

Thus, according to one aspect, the present application provides a method for increasing the immunogenicity of an antigen comprising a) cultivation of mycoplasma bacteria in a serum-reduced or swine serum free, eukaryotic cell system; b) obtaining an antigen of the mycoplasma bacteria; and c) addition of a pharmaceutically acceptable carrier. Preferably, at least one of the mycoplasma antigens is whole inactivated mycoplasma bacterin, preferably inactivated with formalin. It is understood, that only one, some, or all of the mycoplasma antigens can be whole inactivated bacterin.

In one aspect of the present invention the antigen has an increased immunogenicity compared to an antigen obtained from mycoplasma bacteria cultivated in a cell free culturing system. Thus, according to one aspect, the present application provides a method for increasing the immunogenicity of an antigen comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the immunogenic composition has an increased immunogenicity compared to an immunogenic composition comprising the same antigen obtained from mycoplasma bacteria cultivated in a cell free culturing system. Preferably, at least one of the mycoplasma antigens is whole inactivated mycoplasma bacterin, preferably inactivated with formalin. It is understood, that only one, some, or all of the mycoplasma antigens can be whole inactivated bacterin.

The term "increased immunogenicity" as used herein, means that the immunological response caused by an immunogenic composition comprising an antigen of interest is increased as compared to a reference immunogenic composition comprising the same antigen, wherein the antigen of the reference immunogenic composition is prepared of mycoplasma bacteria cultivated in a cell free culturing system.

The term "increased" means, that the cellular and/or antibody mediated immune response is increased by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising the same antigen, wherein the antigen of the reference immunogenic composition is prepared of mycoplasma bacteria cultivated in a cell free culturing system. It is in the general knowledge of a person skilled in the art how to measure the cellular and/or antibody mediated immune response. In particular, it is clear to such person skilled in the art either to compare the cellular mediated immune response of the immunogenic composition of interest with cellular mediated immune response of the reference, or the antibody mediated immune response of the immunogenic composition of interest with that of the reference composition, but neither the cellular mediated immune response of a immunogenic composition of interest with the antibody mediated immune response of the reference or vice versa. Moreover, the cellular mediated immune response can be measured, for example, by measuring the activation of cytotoxic T-cells by an immunogenic composition/antigen of interest. The antibody mediated immune response can be measured, for example, by measuring the amount of antigen specific antibodies, generated in cause of the administration of the immunogenic composition comprising such antigen to an animal. The cellular and/or antibody mediated immune response can be measured, for example, by using a mouse model, a cat model, a cattle model or a swine model. However, the assays as described in Example 4 and 5 shall be used as a reference assay for detecting the immunological response against *M. hyorhinis* and *M. hyopneumoniae*.

The term "same antigen" means, that nature of the antigens is identical. Thus, if the mycoplasma antigen of the immunogenic composition produced in a serum-reduced, eukaryotic cell system is whole inactivated bacterin of *M. hyorhinis*, than the same antigen means that the mycoplasma antigen of the cell-free system is also whole inactivated bacterin of *M. hyorhinis*. Furthermore, if the mycoplasma antigen of the immunogenic composition produced in a serum-reduced, eukaryotic cell system is prepared or purified according to a specific method, than the "same antigen" means that the mycoplasma antigen of the cell-free system is prepared or purified according to the same method.

The term "reference" immunogenic composition refers to an immunogenic composition not obtained by the cultivation of mycoplasma bacteria in a serum-reduced or swine serum-free, eukaryotic cell system according to the present invention.

Rather the term "reference" immunogenic composition refers to an immunogenic composition obtained by the cultivation of mycoplasma bacteria in a cell free culturing system supplemented with serum using the same antigen. The cultivation of mycoplasma bacteria in a cell free culturing system supplemented with serum is well known to the person skilled in the art. The serum origin and the serum concentration are dependent on the mycoplasma bacteria to be cultivated and the yields of mycoplasma bacteria to be obtained. *M. hyorhinis, M. hyopneumoniae* and *M. hyosynoviae* are generally cultivated in a cell free culturing system supplemented with 10-20% (v/v) porcine serum and 5-10% (v/v) yeast extract to obtain high yields. However, it is to be understood that the serum concentrations can be varied, the yeast extract can be deleted and the origin of the serum can be changed, exemplary to fetal calf serum or the like.

The present invention does not only provide methods for the preparation of immunogenic compositions or methods for increasing the immunogenicity of an antigen as defined above, it also relates to an immunogenic composition that is obtainable by the methods as described above. Thus, in a further aspect the present application relates to an immunogenic composition obtainable by a method according to the invention and described herein. In general, such method comprises a) cultivation of mycoplasma bacteria in a serum-reduced or swine serum free, eukaryotic cell system; b) obtaining an antigen of the mycoplasma bacteria; and c) addition of a pharmaceutically acceptable carrier. Preferably, at least one of the mycoplasma antigens is whole inactivated mycoplasma bacterin, preferably inactivated with formalin. It is understood, that only one, some, or all of the mycoplasma antigens can be whole inactivated bacterin.

In one aspect of the present invention the immunogenic composition shows an increased immunogenicity compared to a reference immunogenic composition comprising an antigen, wherein the antigen of the reference immunogenic composition is prepared of a mycoplasma bacteria cultivated in a cell free culturing system.

Thus, according to a further aspect, the present application provides an immunogenic composition obtainable by a method comprising a) cultivation of mycoplasma bacteria in a serum-reduced or swine serum free, eukaryotic cell system; b) obtaining an antigen of the mycoplasma bacteria; and c) addition of a pharmaceutically acceptable carrier. According to a further aspect, such immunogenic composition shows an increased immunogenicity compared to a reference immunogenic composition comprising the same antigen prepared of a mycoplasma bacteria cultivated in a cell free culturing system. Preferably, at least one of the mycoplasma antigens is whole inactivated mycoplasma bacterin, preferably inactivated with formalin. It is understood, that only one, some, or all of the mycoplasma antigens can be whole inactivated bacterin.

In a further aspect, the immunogenic composition comprises components of the eukaryotic cells of said eukaryotic cell system.

The term "components of the eukaryotic cells" comprises both whole cells and fragments of said eukaryotic cells. The term "fragment" comprises any parts of the eukaryotic cell such as parts of the cell membrane or intracellular organelles as a whole or parts thereof. However, the term fragment also encompasses any part of said eukaryotic cell comprising lipids, proteins, sugars, DNA, RNA and the alike as well as combinations thereof. Further, the components of the eukaryotic cells and the mycoplasma antigen can either be in the immunogenic composition separately or attached to each other or a combination thereof.

Thus, according to one aspect, the present application provides an immunogenic composition obtainable by a method comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the immunogenic composition comprises components of the eukaryotic cells of said eukaryotic cell system. Preferably, at least one of the mycoplasma antigens is whole inactivated mycoplasma bacterin, preferably inactivated with formalin. It is understood, that only one, some, or all of the mycoplasma antigens can be whole inactivated bacterin.

In a further aspect, said components of the eukaryotic cells are attached to the mycoplasma antigen.

The term "attached" refers to any interaction, association, binding, adhering or linking of said components of the eukaryotic cells to the mycoplasma antigen. Thus, the term attached encompasses any interactions including indirect or direct, non-reversible or reversible, physical and chemical, electrostatic, and/or covalent bonds. Thus, it has to be understood that the components of the eukaryotic cells, for example, can be bound to the mycoplasma antigen. However, it has to be understood that the components of the eukaryotic cells can also be linked to the mycoplasma antigen(s). Such linking can be produced by several methods well known to the person skilled in the art such as formaldehyde treatment and the like.

Thus, according to one aspect, the present application provides an immunogenic composition obtainable by a method comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein said components of the eukaryotic cells are attached to the mycoplasma antigen. Preferably, at least one of the mycoplasma antigens is whole inactivated mycoplasma bacterin, preferably inactivated with formalin. It is understood, that only one, some or all of the mycoplasma antigens can be whole inactivated bacterin.

Typically, when a bacterial antigen such mycoplasma bacterin is used the immunogenic composition contains an amount of about $10^3$ to about $10^{10}$ colony forming units (CFU) of the bacterial antigen per dose, preferably, about $10^4$ to about $10^9$ CFU of the bacterial antigen per dose, more preferably about $10^5$ to about $10^6$ CFU of the bacterial antigen per dose. If inactivated bacterin is used in the immunogenic composition, the CFU values refer to the amount of mycoplasma bacteria prior to inactivation.

For example, the immunogenic composition of the present invention comprising antigens of *M. hyopneumoniae* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose. The immunogenic composition of the present invention comprising antigens of *M. hyorhinis* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose. The immunogenic composition of the present invention comprising antigens of *M. hyosynoviae* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose.

Thus, according to one aspect, the present application provides method for providing an immunogenic composition comprising a) cultivation of mycoplasma bacteria in a serum-reduced or swine serum free, eukaryotic cell system; b) obtaining an antigen of the mycoplasma bacteria; and c) addition of a pharmaceutically acceptable carrier, wherein the immunogenic composition contains an amount of about $10^3$ to about $10^{10}$ colony forming units (CFU) of the bacterial antigen per dose. Preferably, at least one of the mycoplasma antigens is whole inactivated mycoplasma bacterin, preferably inactivated with formalin. It is understood, that only one, some or all of the mycoplasma antigens can be whole inactivated bacterin.

It is understood by a person skilled in the art, that the various process steps of the methods for providing an immunogenic composition as described herein can be combined to practice the invention as described herein.

EXAMPLES

The following examples are only intended to illustrate the present invention. They shall not limit the scope of the claims in any way.

Example 1

Cultivation of *Mycoplasma* Bacteria in MDCK Cells or McCoy Cell, Respectively

A. Cultivation of *M. hyorhinis*, *M. Hyosynoviae* and *M. hyopneumoniae* in MDCK Cells

*M. hyorhinis*:

Confluent T75 flask(s) of MDCK cells are trypsinized and subcultured into 5, T150 flasks (1:10 split) using MEM+5% FBS. Flasks are incubated at 37° C.+5% $CO_2$ until an approximately 95-100% confluent monolayer is observed. Media is decanted and flasks rinsed twice with 1×PBS. Four-five mls of *M. hyorhinis* is added to each flask (MOI=10-100). Confluent cells in flasks are infected under the same incubation conditions as above for no less than 2 hours. After the infection period, sufficient Infection Media (MEM+2% FBS), pre-warmed to approximately 37° C., is added to each flask for a total volume of 60 ml per flask. Flasks are incubated until >90% CPE (approximately 3-7 days). Cell suspensions are collected from each flask and pooled together (Passage=n). The pooled material is used to infect new flasks of approximately 95-100% confluent MDCK cells in the same manner as the previous infection (Passage=n+1), increasing the number of flasks used to achieve a sufficient final volume as deemed necessary (Passage=n+2, Passage=n+3, etc).

*M. hyosynoviae*:

*M. hyosynoviae* is cultured in the same manner as *M. hyorhinis* with a few modifications: Infection Media contains DMEM+2% FBS+1% arginine solution; *M. hyosynoviae* does not typically exhibit CPE so color change and turbidity of the media is the key indicator to subculture to the next passage.

*M. hyopneumoniae*:

*M. hyopneumoniae* is cultured in the same manner as *M. hyorhinis*. Depending on the strain used for infection, CPE may or may not be present. Therefore, color change and turbidity of media can be used as the indicator to subculture to the next passage.

B. Cultivation Conditions for *M. hyorhinis*, *M. Hyosynoviae* and *M. hyopneumoniae* in McCoy Cells.

*M. hyorhinis*:

McCoy cells are grown as suspension cultures in stir flasks in modified EMEM supplemented with 10% FBS. Cells are subcultured by seeding new flasks so as to have a final concentration of $10^5$-$10^6$ cells/ml. For *M. hyorhinis*, a 500 ml cell suspension at a concentration of $10^5$-$10^6$ cells/ml in a 3 L flask is seeded with 1 ml $10^7$-$10^8$ CFUs. Flasks are incubated at 37° C. in the presence of 5% $CO_2$ on a magnetic stir plate for 3-7 days. *Mycoplasma* growth is ascertained by visible acidic pH change and increase in turbidity. *Mycoplasma* growth is also evaluated by PFU assays to determine counts.

*M. hyosynoviae*:

*M. hyosynoviae* is cultivated in a similar manner as *M. hyorhinis*. A 500 ml cell suspension at a concentration of $10^5$-$10^6$ cells/ml in a 3 L flask is seeded with 1 ml $10^5$-$10^7$ CFUs. Flasks are then incubated at 37° C. in the presence of 5% $CO_2$ on a magnetic stir plate for approximately 2 weeks. Both pH change and increase in turbidity are used to determine growth in addition PFU assays to determine counts.

*M. hyopneumoniae*:

*M. hyopneumoniae* is cultivated in a similar manner as *M. hyorhinis* and *M. hyosynoviae*. A 500 ml cell suspension at a concentration of $10^5$-$10^6$ cells/ml in a 3 L flask is seeded with 1 ml $10^5$-$10^7$ CFUs. Flasks are incubated at 37° C. in the presence of 5% $CO_2$ on a magnetic stir plate for approximately 2 weeks. Both pH change and increase in turbidity can be used to determine growth in addition to PFU assays to determine counts.

C. Cultivation of *Mycoplasma* Species with Various Serum Types

To evaluate whether a *mycoplasma* species can be cultivated in serum from different species, MDCK cells are infected with *M. hyorhinis* and cultured in either Fetal Bovine Serum, Porcine Serum, Rabbit Serum, Chicken Serum or Horse Serum. For each serum type, the cultivation of *M. hyorhinis* in MDCK cells is performed as described above (i.e., 5% serum for cell growth and 2% serum for infection). *M. hyorhinis* is harvested at four days post-infection per standard method. A CCU (color changing unit) assay is performed to determine the live titer of *M. hyorhinis*. Further, a qPCR (quantitative real time Poylmerase chain reaction) is performed to determine the total genomic content of *M. hyorhinis*. An exemplary experiment is shown in Table 1.

TABLE 1

Cultivation of *M. hyorhinis* with various serum types

| Serum type | qPCR log (gc/µl) | CCU50 (log/ml) |
|---|---|---|
| Fetal Bovine Serum | 6.15 | 8.00 |
| Porcine Serum | 6.06 | 8.50 |
| Rabbit Serum | 6.11 | 8.33 |
| Chicken Serum | 6.31 | 8.00 |
| Horse Serum | 6.49 | 9.00 |

Table 1 demonstrates that the titers measured either by CCU assay or qPCR are similar for the various serum types. Further, western blot data (not shown) support this data. Thus, *M. hyorhinis* can be cultivated in MDCK cells irrespective of which serum type is used for cultivation.

Example 2

Preparation of Vaccines

When final passage is ready to harvest (>90% CPE present), a single freeze-thaw cycle is performed on all flasks by placing them into a <−60° C. freezer for >2 hours, quickly thawing at 37° C., collecting and pooling lysate, and pipetting up and down several times to homogenize. Generally, 10-20% glycerol is then added to the suspension and homogenized. The suspension is aliquoted into working volumes. Stocks are kept at <−60° C. until needed.

Appropriate volumes of the above stocks are inactivated with 0.2% formalin. Excess formalin is neutralized with sodium bisulfite at the time of vaccine blending. Vaccines are blended with Montanide™ ISA 207 VG adjuvant or with CARBOPOL® adjuvant. Vaccines are stored at 2-7° C.

Example 3

Assessment of Effectiveness of the Vaccines

The efficacy of vaccines is evaluated based on the ability to induce an antibody response (as well as the titer by ELISA) after administration in swine.

Animal Care:

Animals are in good health and nutritional status before a study is initiated. Prior to the randomization procedure a health examination is conducted. Non-medicated feed is used throughout the duration of the study. Feed rations are appropriate for the age, condition, and species of test animal according to facility standard operating procedure. Water is provided ad libitum throughout the study.

Assessment of Effectiveness of M. hyorhinis and M. hyopneumoniae Vaccines after Administration in Swine.

M. hyorhinis:

On D0 and again on D21, conventional piglets of 6 weeks±5 days of age are administered a 2 ml dose (7.1-7.3 log 10 CCU/dose) of M. hyorhinis vaccine intramuscularly. M. hyorhinis is prepared as above; i.e., cultured in MDCK cells as described above. The vaccine is adjuvanted with Montanide ISA207VG or CARBOPOL®. PBS is used as Placebo. The pigs are observed daily for general health. Blood is collected prior to vaccination at D0, 7, 14, 21, 28, 35 and 42. The serum is tested for M. hyorhinis specific antibodies by BIVI R&D Indirect ELISA. For the BIVI R&D ELISA, an S/P ratio of >0.200 is considered positive.

In the example shown in Table 2, the M. hyorhinis ELISA indicates a strong antibody response. Six/six (100%) animals vaccinated with M. hyorhinis-MDCK+Montanide ISA207VG were positive two weeks after the first dose (D14). All animals remained positive through D42, with a boost in titers noted one week after the second dose (D28). Animals vaccinated with M. hyorhinis-MDCK+CARBOPOL® also show an antibody response.

TABLE 2

| | M. hyorhinis ELISA results | | | | | | | |
|---|---|---|---|---|---|---|---|---|
| | Pre | D0 | D7 | D14 | D21 | D28 | D35 | D42 |
| M. hyorhinis MDCK + Montanide ISA207VG | 0.00 | 0.003 | 0.043 | 0.972 | 1.123 | 1.340 | 1.152 | 1.133 |
| M. hyorhinis MDCK + CARBOPOL ® | 0.002 | 0.018 | 0.059 | 0.095 | 0.122 | 0.354 | 0.375 | 0.409 |
| Placebo (PBS) | 0.001 | 0.005 | 0.011 | 0.015 | 0.021 | 0.031 | 0.057 | 0.070 |

Similar antibody response results post-vaccination were achieved using M. hyorhinis cultured in McCoy cells (data not shown). Similar results were obtained after a single dose administration (data not shown).

M. hyopneumoniae:

On D0 and again on D21 conventional piglets of 6 weeks±5 days of age are administered a 2 ml dose (8.0-8.5 log 10 CCU/dose) of M. hyopneumoniae vaccine intramuscularly. The vaccine is adjuvanted with Montanide ISA207VG. PBS is used as Placebo. The pigs are observed daily for general health. Blood is collected prior to vaccination at D0, 7, 14, 21, 28, 35 and 42 to test for the presence of M. hyopneumoniae antibodies. In one example, a commercial IDEXX ELISA was used. For the IDEXX ELISA, an S/P ratio of >0.400 was considered positive.

In the example shown in Table 3, the M. hyopneumoniae ELISA indicated a strong antibody response. For the M. hyopneumoniae MDCK+ISA207 vaccinated animals, 3/6 (50%) animals were positive on D14 and 5/6 (83.3%) on D21 with 6/6 (100%) positive on D28, 35, and 42.

TABLE 3

| | M. hyopneumoniae IDEXX ELISA results | | | | | | | |
|---|---|---|---|---|---|---|---|---|
| | Pre | D0 | D7 | D14 | D21 | D28 | D35 | D42 |
| M. hyopneumoniae MDCK + Montanide ISA207VG | −0.024 | −0.022 | 0.034 | 0.601 | 0.949 | 1.775 | 1.986 | 1.895 |
| Placebo (PBS) | −0.019 | 0.011 | −0.021 | −0.015 | −0.025 | −0.025 | 0.016 | 0.016 |

Similar results were obtained after a single dose administration, data not shown.

Example 4

Effectiveness of Vaccines Obtained from Mycoplasma Bacteria Cultured in a Eukaryotic Cell Line Versus Vaccines Obtained from Mycoplasma Bacteria Cultured in a Cell Free System Fifty-four CD/CD animals at 8 weeks±5 days of age are divided into six groups. Group V1 and V2 each receive an inactivated MHRN001 isolate of M. hyorhinis cultured in MDCK cells and CM (complex medium; such as proteose peptone based medium containing porcine serum and yeast extract or Friis-based media), respectively; Group V3 and V4 receive an inactivated MHRN002 isolate of M. hyorhinis cultured in MDCK cells and CM, respectively. All vaccines are adjuvanted with Montanide ISA207VG; dosage and route were 2×2 ml doses by intramuscular injection with one dose on D0 and the second on D21. Group CC (control group) receive an antigen-free placebo (PBS) in the same fashion. Group SC (strict control) receive no treatment throughout the study, serving as strict control animals. On D42, 43, and 44, pigs in Group V1-V4 and CC are challenged with a virulent *M. hyorhinis*. Dosage and route of administration is 40 ml intraperitoneal, 15 ml intravenous, and 15 ml intranasal, respectively. Blood is collected weekly from D0 through the end of the study (D58) for *M. hyorhinis*-specific ELISA testing. For the R&D *M. hyorhinis* ELISA, an S/P ratio of >0.200 was considered positive. In the exemplary study shown in Table 4, all pigs in Group SC remained negative throughout the study, indicating a lack of exposure to *M. hyorhinis*. Groups V I-V4 and CC were negative on D0 and 7. However, serology results varied between the CM-based and MDCK-based vaccines. When compared to the CM-based vaccines, the MDCK-based vaccines showed earlier on-set of sero-conversion, greater numbers of sero-positive pigs, and higher serological titers.

TABLE 4

*M. hyorhinis* ELISA results
*M. hyorhinis* ELISA Average S/P Ratios by Group

| Group | D0 | D7 | D14 | D21 | D28 | D35 | D42 | D49 | D58 |
|---|---|---|---|---|---|---|---|---|---|
| MHRN001- | −0.002 | 0.010 | 0.199 | 0.482 | 0.916 | 0.971 | 0.929 | 1.056 | 0.991 |
| MHRN001- | 0.001 | 0.009 | 0.031 | 0.081 | 0.395 | 0.401 | 0.370 | 0.793 | 0.770 |
| MHRN002 MDCK (V3) | 0.004 | 0.014 | 0.157 | 0.424 | 0.981 | 1.023 | 0.953 | 1.097 | 1.086 |
| MHRN002-CM (V4) | 0.003 | 0.011 | 0.017 | 0.047 | 0.298 | 0.299 | 0.263 | 0.704 | 0.608 |
| Placebo (CC) | 0.004 | 0.004 | 0.009 | 0.023 | 0.021 | 0.029 | 0.031 | 0.262 | 0.433 |
| Strict Control (SC) | −0.003 | −0.002 | −0.003 | 0.005 | 0.008 | 0.015 | 0.021 | 0.031 | 0.060 |

Titration experiments are performed to compare cell culture-based vaccines to vaccines from mycoplasma bacteria cultured in a cell free system.

*M. hyorhinis* is cultured in McCoy cells as described above or cultured in CM (complex medium), respectively.

Vaccines are made with McCoy antigen using undiluted antigen (full), 1:10 antigen, and 1:100 antigen, all blended 1:1 with Montanide ISA207VG as adjuvant. Vaccines using CM derived antigen are made in the same manner.

Pigs (three weeks of age at the time of vaccination) are vaccinated with a single 2 mL dose administered IM on Day 0.

As shown in Table 5, group averages from the exemplary study were all "negative" prior to challenge (D0-D21), though, the "McCoy+ISA full" and "McCoy+ISA 1:10" showed responses trending towards positive. At one week post-challenge (D28), all vaccinate groups responded with the exception of CM 1:100.

From Table 5 it is apparent that each antigen type (McCoy, CM) exhibits a standard titration effect (Full>1:10>1:100). Further, from Table 5 it is apparent that the "McCoy+ISA full" and "McCoy+ISA 1:10" vaccinates have higher average scores than the "CM+ISA full" antigen, and that holds true through termination at D42. Groups with positive (S/P≥0.200) averages post-challenge are the "McCoy+ISA full" and the "McCoy+ISA 1:10" groups. The McCoy Full vaccine and 1:10 dilution showed a higher sero-response than CM Full vaccine both pre-challenge and post-challenge. Furthermore, animals vaccinated with McCoy 1:100 also demonstrated a response distinguishable from placebo (non-vaccinates) and CM 1:100 groups (CM 1:100 response, or lack thereof, was equivalent to non-vaccinates). The titration experiments demonstrated that cell culture-based vaccines had better serological results compared to vaccines from mycoplasma bacteria cultured in a cell free system.

TABLE 5

*M. hyorhinis* ELISA results
*M. hyorhinis* ELISA Average S/P Ratios by Group

| Group | D0 | D7 | D14 | D21 | D28 | D35 | D42 |
|---|---|---|---|---|---|---|---|
| McCoy + ISA full | 0.002 | 0.012 | 0.032 | 0.117 | 0.312 | 0.298 | 0.325 |
| McCoy + ISA 1:10 | 0.000 | 0.005 | 0.065 | 0.107 | 0.291 | 0.193 | 0.221 |
| McCoy + ISA 1:100 | 0.001 | 0.001 | −0.001 | 0.000 | 0.145 | 0.118 | 0.150 |
| CM + ISA full | 0.002 | 0.009 | 0.011 | 0.034 | 0.190 | 0.163 | 0.190 |
| CM + ISA 1:10 | −0.001 | 0.017 | 0.003 | 0.014 | 0.114 | 0.132 | 0.176 |

TABLE 5-continued

*M. hyorhinis* ELISA results
*M. hyorhinis* ELISA Average S/P Ratios by Group

| Group | D0 | D7 | D14 | D21 | D28 | D35 | D42 |
|---|---|---|---|---|---|---|---|
| CM + ISA 1:100 | −0.002 | 0.000 | −0.002 | 0.001 | 0.019 | 0.043 | 0.093 |
| Placebo: PBS + ISA | −0.001 | 0.002 | −0.002 | −0.002 | 0.021 | 0.039 | 0.081 |
| Strict Control | −0.002 | −0.001 | −0.002 | −0.002 | −0.002 | 0.008 | 0.024 |

The invention claimed is:

1. A method for preparing an immunogenic composition for the treatment of *mycoplasma* infections in a subject comprising:
   co-cultivating a *mycoplasma* bacteria with MDCK cells in serum-reduced conditions to obtain a bacterin comprising a *mycoplasma* antigen, wherein the *mycoplasma* bacteria comprises at least one *mycoplasma* species selected from *Mycoplasma* hyorhinis, *Mycoplasma* hyosynoviae, and *Mycoplasma* hyopneumoniae; and
   adding a pharmaceutically acceptable carrier to the bacterin.

2. The method of claim 1, wherein the *mycoplasma* bacteria are cultivated in the absence of serum.

3. The method of claim 1, wherein the *mycoplasma* antigen has an increased immunogenicity compared to an antigen obtained from *mycoplasma* bacteria cultivated in a cell free culturing system.

4. The method of claim 1, wherein the bacterin has been inactivated with formalin or binary ethylenimine.

5. The method of claim 1, wherein the *mycoplasma* bacteria comprises at least two *mycoplasma* species selected from *Mycoplasma* hyorhinis, *Mycoplasma* hyosynoviae, and *Mycoplasma* bovis.

6. The method of claim 1, wherein the *mycoplasma* bacteria comprises *Mycoplasma* hyopneumoniae, *Mycoplasma* hyorhinis, and *Mycoplasma* hyosynoviae.

7. The method of claim 1, wherein said immunogenic composition is formulated for a single-dose administration.

8. The method of claim 1, wherein said pharmaceutically acceptable carrier is a solvent, a dispersion media, a coating, a stabilizing agent, a diluent, a preservative, an antibacterial agent, an antifungal agent, an isotonic agent, an adsorption delaying agent, an adjuvant, an immune stimulant, or any combinations thereof.

9. The method of claim 1, wherein said pharmaceutically acceptable carrier is an adjuvant selected from aluminum hydroxide, aluminum phosphate, a saponin, a water-in-oil emulsion, an oil-in-water emulsion, a water-in-oil-in-water emulsion, a polymer of acrylic or methacrylic acid, a copolymer maleic anhydride and alkenyl derivative, an MI adjuvant system, a Block co-polymer, SAF-M, monophosphoryl lipid A, Avridine lipid-amine, heat-labile enterotoxin from *E. coli* (recombinant or otherwise), cholera toxin, IMS 1314, muramyl dipeptide, or any combinations thereof.

10. The method of claim 1, wherein said pharmaceutically acceptable carrier is a water-in-oil-in-water emulsion or a carbomer.

11. The method of claim 6, wherein the *mycoplasma* bacteria further comprises *Mycoplasma* bovis.

* * * * *